(12) United States Patent
Hiraoka et al.

(10) Patent No.: US 9,604,199 B2
(45) Date of Patent: Mar. 28, 2017

(54) CATALYST FOR PRODUCTION OF BUTADIENE, PROCESS FOR PRODUCING THE CATALYST, AND PROCESS FOR PRODUCING BUTADIENE USING THE CATALYST

(71) Applicant: NipponKayaku KabushikiKaisha, Tokyo (JP)

(72) Inventors: Ryota Hiraoka, Yamaguchi (JP); Yumi Hino, Yamaguchi (JP); Kimito Okumura, Tokyo (JP); Hiroki Motomura, Yamaguchi (JP)

(73) Assignee: NipponKayaku KabushikiKaisha, Tokyo (JP)

( * ) Notice: Subject to any disclaimer, the term of this patent is extended or adjusted under 35 U.S.C. 154(b) by 0 days.

(21) Appl. No.: 14/396,483

(22) PCT Filed: Apr. 19, 2013

(86) PCT No.: PCT/JP2013/061623
§ 371 (c)(1),
(2) Date: Oct. 23, 2014

(87) PCT Pub. No.: WO2013/161702
PCT Pub. Date: Oct. 31, 2013

(65) Prior Publication Data
US 2015/0328623 A1 Nov. 19, 2015

(30) Foreign Application Priority Data
Apr. 23, 2012 (JP) ................. 2012-098259

(51) Int. Cl.
| | | |
|---|---|---|
| *B01J 23/88* | (2006.01) | |
| *B01J 23/887* | (2006.01) | |
| *B01J 35/02* | (2006.01) | |
| *B01J 35/08* | (2006.01) | |
| *B01J 37/00* | (2006.01) | |
| *B01J 37/02* | (2006.01) | |
| *B01J 37/03* | (2006.01) | |
| *C07C 45/35* | (2006.01) | |
| *C07C 51/25* | (2006.01) | |
| *C07C 5/48* | (2006.01) | |
| *B01J 23/00* | (2006.01) | |
| *B01J 23/888* | (2006.01) | |
| *B01J 23/889* | (2006.01) | |
| *B01J 35/10* | (2006.01) | |

(52) U.S. Cl.
CPC ......... *B01J 23/8876* (2013.01); *B01J 23/002* (2013.01); *B01J 23/8878* (2013.01); *B01J 23/8885* (2013.01); *B01J 23/8898* (2013.01); *B01J 35/08* (2013.01); *B01J 35/1038* (2013.01); *C07C 5/48* (2013.01); *B01J 2523/00* (2013.01); *C07C 2521/12* (2013.01); *C07C 2523/04* (2013.01); *C07C 2523/18* (2013.01); *C07C 2523/28* (2013.01); *C07C 2523/745* (2013.01); *C07C 2523/75* (2013.01); *C07C 2523/755* (2013.01); *C07C 2523/883* (2013.01); *C07C 2523/887* (2013.01)

(58) Field of Classification Search
CPC ... B01J 21/00; B01J 23/31; B01J 23/84; B01J 23/85; B01J 23/88; B01J 23/881; B01J 23/882; B01J 23/883; B01J 23/887; B01J 23/8876; B01J 37/0223; B01J 37/0045; B01J 37/0038; B01J 35/026; B01J 35/08; C07C 45/35; C07C 51/252
USPC .................. 502/306–317, 119, 321–324, 439
See application file for complete search history.

(56) References Cited

U.S. PATENT DOCUMENTS

| | | | |
|---|---|---|---|
| 4,419,267 A | 12/1983 | Sasaki et al. | |
| 5,072,052 A | 12/1991 | Boeck et al. | |
| 6,028,220 A | 2/2000 | Wada et al. | |
| 6,509,508 B2 * | 1/2003 | Kimura ................. | B01J 23/002 562/537 |
| 6,740,769 B1 * | 5/2004 | Mizutani .............. | B01J 23/8876 502/110 |
| 6,781,013 B2 * | 8/2004 | Tanimoto ............... | B01J 23/002 562/532 |

(Continued)

FOREIGN PATENT DOCUMENTS

| | | |
|---|---|---|
| CA | 903079 A | 6/1972 |
| CN | 1050181 A | 3/1991 |
| CN | 101990460 A | 3/2011 |
| EP | 2298446 A1 | 3/2011 |
| EP | 2617491 A1 | 7/2013 |
| EP | 2842625 A1 | 3/2015 |
| EP | 2842626 A1 | 3/2015 |
| JP | 43-27742 B | 11/1968 |
| JP | 49-3498 B | 1/1974 |

(Continued)

OTHER PUBLICATIONS

International Search Report and Written Opinion mailed May 21, 2013 in corresponding PCT application No. PCT/JP2013/061624.

(Continued)

*Primary Examiner* — Cam N. Nguyen
(74) *Attorney, Agent, or Firm* — Nields, Lemack & Frame, LLC

(57) ABSTRACT

A catalyst for producing butadiene using n-butene as a raw material, a process for producing the same and a process for producing butadiene using the catalyst are provided, and specifically, a catalyst for producing butadiene by gas-phase contact oxidative dehydrogenation of n-butene, which is capable of stably producing butadiene in a high yield from the beginning of the reaction, a process for producing the same and a process for producing butadiene, in which the catalyst is a shaped catalyst containing a complex metal oxide having molybdenum as an essential ingredient, wherein the pore volume of macropores is 80% or more, more preferably 90% or more, based on the total pore volume, are provided.

9 Claims, No Drawings

(56) References Cited

U.S. PATENT DOCUMENTS

| | | | | |
|---|---|---|---|---|
| 6,784,134 B2* | 8/2004 | Kasuga | ............ | B01J 23/002 428/364 |
| 6,878,847 B2* | 4/2005 | Kasuga | ............ | B01J 23/002 502/185 |
| 2005/0239643 A1 | 10/2005 | Benderly et al. | | |
| 2011/0034330 A1 | 2/2011 | Czaja et al. | | |
| 2011/0144406 A1 | 6/2011 | Masatsugu et al. | | |
| 2012/0130137 A1 | 5/2012 | Orita et al. | | |
| 2013/0172615 A1 | 7/2013 | Kawano et al. | | |
| 2015/0126774 A1 | 5/2015 | Hiraoka et al. | | |

FOREIGN PATENT DOCUMENTS

| | | | |
|---|---|---|---|
| JP | 56-163756 A | 12/1981 | |
| JP | 58-188823 A | 11/1983 | |
| JP | 3775872 B | 5/2006 | |
| JP | 2011-518659 A | 6/2011 | |
| JP | 2011-178719 A | 9/2011 | |
| JP | 2011-219366 A | 11/2011 | |
| JP | 2011-246384 A | 12/2011 | |
| JP | 2012-45516 A | 3/2012 | |
| JP | 5130562 B | 1/2013 | |
| KR | 1019990077024 A | 10/1999 | |
| KR | 1020120026049 A | 3/2012 | |
| TW | 200539939 A | 12/2005 | |
| TW | 201100372 A | 1/2011 | |
| WO | 2012036038 A1 | 3/2012 | |
| WO | 2015053269 A1 | 4/2015 | |

OTHER PUBLICATIONS

International Search Report and Written Opinion mailed Nov. 6, 2014 in corresponding PCT application No. PCT/JP2013/061624.
International Search Report and Written Opinion mailed May 21, 2013 in corresponding PCT application No. PCT/JP2013/061623.
International Preliminary Report on Patentability mailed Nov. 6, 2014 in corresponding PCT application No. PCT/JP2013/061623.
Japanese communication, with English translation, dated Jan. 26, 2016 in co-pending Japanese patent application No. 2014-512523.
Taiwanese communication, with English translation, dated Jan. 26, 2016 in co-pending Taiwanese patent application No. 102114342.
Office action mailed Apr. 15, 2016 in co-pending U.S. Appl. No. 14/396,478.
Chinese communication, with English translation, dated Apr. 12, 2016 in corresponding Chinese patent application No. 201380021493.0.
Saudi Arabian communication, with English translation, dated May 6, 2015 in co-pending Saudi Arabian patent application No. 113340492.
Chinese communication, with English translation, dated Aug. 25, 2015 in co-pending Chinese patent application No. 201380021431.X.
European communication dated Sep. 24, 2015 in co-pending European patent application No. 13782624.4.
European communication dated Sep. 24, 2015 in corresponding European patent application No. 13782374.6.
Sommer, et al., "Auslegung von Granulierteller und Granuliertrommel", Chemie Ingenieur Technik, vol. 50, No. 7, Jan. 1, 1978, p. 518-524.
Office action mailed Oct. 28, 2015 in co-pending U.S. Appl. No. 14/396,478.
Saudi Arabian communication, with English translation, dated Aug. 9, 2015 in co-pending Saudi Arabian patent application No. 11340492.
Korean communication, with English translation, dated Nov. 17, 2016 in co-pending Korean patent application No. 10-2014-7029775.
Taiwanese communication, with English translation, dated Jul. 1, 2016 in co-pending Taiwanese patent application No. 102114335.
Office action mailed Jun. 23, 2016 in co-pending U.S. Appl. No. 14/396,478.
Notice of Allowance mailed Oct. 3, 2016 in co-pending U.S. Appl. No. 14/396,478.
Notice of Allowance mailed Oct. 18, 2016 in co-pending U.S. Appl. No. 14/396,478.

* cited by examiner

CATALYST FOR PRODUCTION OF BUTADIENE, PROCESS FOR PRODUCING THE CATALYST, AND PROCESS FOR PRODUCING BUTADIENE USING THE CATALYST

TECHNICAL FIELD

The present invention relates to a catalyst for stably producing butadiene from n-butene under a high conversion and a high yield from the beginning of the reaction, a process for producing the catalyst, and a process for producing butadiene using the catalyst.

BACKGROUND ART

The butadiene is an important chemical to be used as a raw material for synthetic rubbers and the synthetic rubbers are used in a large quantity for automobile tires and the like. Almost all of the butadiene is produced by a cracking process of oil. It is produced by extracting and separating butadiene from C4 fractions comprising isobutene, n-butene, butadiene, and the like. A demand for energy-saving type automobile tires using butadiene as a raw material has rapidly increased owing to global augmentation in demand for automobiles and increase in awareness of environmental issues in recent years. Further, the demand for butadiene has continued to greatly exceed the production from the C4 fraction owing to decrease in operation rate of naphtha crackers and use of petrochemical raw materials derived from natural gas, and therefore, a development of a new production process of butadiene has been desired.

There is known a process for producing butadiene from n-butene that remains from the extraction of butadiene. For example, in Patent Documents 1 and 2, processes of oxidative dehydrogenation in the presence of a complex metal oxide catalyst containing molybdenum, bismuth, iron, and cobalt as main ingredients are described. However, from the standpoints of catalyst activity, selectivity for butadiene, stability of reaction operation, catalyst life, catalyst production, and the like, conventional catalysts are industrially insufficient, and therefore, an improvement thereof has been desired.

The catalyst life of the reaction and the instability of the reaction operation are considered to be due to the carbon content that accumulates on the catalyst. In Patent Document 3, it is described that the accumulation of the carbon content can be suppressed by diluting the catalyst with an inert solid matter and thereby controlling a successive reaction of the product. However, the accumulation of the carbon content cannot be sufficiently suppressed by this method, and besides, a reduction of yield accompanying a decrease in an amount of an active ingredient occurs and a cost for mixing the active ingredient with the inert solid matter takes, and therefore, this method is industrially disadvantageous.

In Patent Document 4, it is described that a high conversion and a high selectivity are maintained for a long period of time by mixing a slight amount of silica into a known catalyst-active ingredient composition, but it has a disadvantage that the catalyst is difficult to produce stably in an industrial scale.

Moreover, in Patent Document 5, there is a description with respect to a coat-shaped catalyst, in which a pore-forming agent is mixed into a catalyst precursor, as well as the production thereof in an industrial scale. However, there is no clear description with respect to an effect on the conversion of butene and the selectivity for butadiene resulting from the production of the coat-shaped catalyst at which a pore-forming agent is mixed.

Thus, from the standpoints of catalyst performance, catalyst life, and operation control in a plant, conventional catalysts do not necessarily afford sufficient performance as industrial catalysts, and further improvement thereof has been desired.

BACKGROUND ART DOCUMENT

Patent Document

[Patent Document 1] JP-B-49-003498
[Patent Document 2] JP-A-58-188823
[Patent Document 3] JP-A-2011-219366
[Patent Document 4] JP-A-2011-178719
[Patent Document 5] JP-T-2011-518659

SUMMARY OF INVENTION

Problem that Invention is to Solve

Therefore, an object of the present invention is to provide a catalyst capable of stably producing butadiene from n-butene in a high yield from the beginning of the reaction, a process for industrially producing the catalyst, and a process for producing butadiene using the catalyst.

Means for Solving Problem

As a result of extensive studies to achieve the above object, the present inventors have found that butadiene can be stably produced from n-butene in a high yield from the beginning of the reaction by using a shaped catalyst of a complex metal oxide having molybdenum as an essential ingredient, wherein the pore volume of macropores of the shaped catalyst is 80% or more, preferably 90% or more based on the total pore volume. Thus, they have accomplished the present invention.

Namely, the present invention relates to the followings.

(1) A shaped catalyst of a complex metal oxide having molybdenum as an essential ingredient, which is a shaped catalyst used in production of butadiene by a gas-phase contact oxidative dehydrogenation reaction of n-butene in the presence of molecular oxygen, wherein pore volume of macropores of the shaped catalyst is 80% or more based on a total pore volume.

(2) The shaped catalyst as described in (1), wherein the pore volume of macropores of the shaped catalyst is 90% or more based on the total pore volume.

(3) The shaped catalyst as described in (1) or (2), wherein the total pore volume is 0.1 ml/g or more and 0.4 ml/g or less.

(4) The shaped catalyst as described in any one of (1) to (3),
wherein the complex metal oxide has a composition represented by the following formula (1):

$$Mo_aBi_bNi_cCo_dFe_fX_gY_hO_x \qquad \text{Formula (1)}$$

wherein Mo, Bi, Ni, Co, Fe and O represents molybdenum, bismuth, nickel, cobalt, iron and oxygen, respectively;
X represents at least one element selected from the group consisting of tungsten, antimony, tin, zinc, chromium, manganese, magnesium, silicon, aluminum, cerium, tellurium, boron, germanium, zirconium and titanium;

Y represents at least one element selected from the group consisting of potassium, rubidium, calcium, barium, thallium and cesium;

a, b, c, d, f, g, h and x represents numbers of atoms of molybdenum, bismuth, nickel, cobalt, iron, X, Y and oxygen, respectively, and a=12, b=0.1 to 7, c+d=0.5 to 20, f=0.5 to 8, g=0 to 2, h=0.005 to 2, and x=a value determined depending on oxidation states of individual elements.

(5) The shaped catalyst as described in any one of (1) to (4), which is a spherical coat-shaped catalyst in which the complex metal oxide is supported on an inert spherical support.

(6) The shaped catalyst as described in (5), wherein powder of the complex metal oxide is supported by a tumbling granulation method.

(7) A process for producing the coat-shaped catalyst as described in (5), wherein powder of the complex metal oxide is supported by a tumbling granulation method.

(8) A process for producing butadiene by using the shaped catalyst as described in any one of (1) to (6) and subjecting n-butene to gas-phase contact oxidative dehydrogenation in the presence of molecular oxygen.

(9) The process for producing butadiene as described in (8), wherein a change between ΔT within one hour from start of reaction and ΔT after two hours is 20° C. or less.

(10) The process for producing butadiene as described in (8) or (9), wherein the shaped catalyst as described in any one of (1) to (6) is used and a change between ΔT within one hour from start of reaction and ΔT after two hours is 10° C. or less.

Effects of Invention

According to the catalyst and the production process of the catalyst in the present invention, a process for stably producing butadiene from n-butene in a high yield from the beginning of the reaction and a catalyst to be suitably used for the process are provided.

MODE FOR CARRYING OUT INVENTION

In the following, the embodiments will be described in detail regarding a catalyst for production of butadiene according to the present invention and a process for producing the catalyst, and a process for producing butadiene using the catalyst of the invention.

The invention is a shaped catalyst of a complex metal oxide having molybdenum as an essential ingredient, the catalyst being capable of being used for a fixed bed multi-tubular reactor, which is a shaped catalyst to be used for producing butadiene from n-butene by a gas-phase contact oxidation in the presence of molecular oxygen, wherein, among the macropore distribution of the shaped catalyst, the pore volume of macropores of the shaped catalyst is 80% or more based on the total pore volume and is preferably 90% or more.

The catalyst to be used in the invention can be prepared by a known process, and it is a catalyst of a complex metal oxide having molybdenum as an essential ingredient. Preferable constituent elements of the catalyst and composition ratio thereof can be represented by the following general formula (1):

    Formula (1)

wherein Mo, Bi, Ni, Co, Fe and O represents molybdenum, bismuth, nickel, cobalt, iron and oxygen, respectively; X represents at least one element selected from the group consisting of tungsten, antimony, tin, zinc, chromium, manganese, magnesium, silicon, aluminum, cerium, tellurium, boron, germanium, zirconium and titanium; Y represents at least one element selected from the group consisting of potassium, rubidium, calcium, barium, thallium and cesium; a, b, c, d, f, g, h and x represents numbers of atoms of molybdenum, bismuth, nickel, cobalt, iron, X, Y and oxygen, respectively, and a=12, b=0.1 to 7, preferably b=0.5 to 4, c+d=0.5 to 20, preferably c+d=1 to 12, f=0.5 to 8, preferably f=0.5 to 5, g=0 to 2, preferably g=0 to 1, h=0.005 to 2, preferably h=0.01 to 0.5 and x=a value determined depending on oxidation states of individual elements.

Here, the raw material mixed liquid and/or the mixed liquid containing the complex metal oxide as a catalyst-active ingredient are prepared by a known method such as a co-precipitation method. As raw materials used on that occasion, nitrate salts, ammonium salts, hydroxides, oxides, acetate salts, and the like of various metal elements such as molybdenum, bismuth, nickel, cobalt, iron, and X and Y described in the above composition formula can be used without particular limitation. It is also possible to obtain a mixed liquid containing a complex metal oxide having different compositions by changing the kind and/or amount of the metal salts to be supplied.

As a drying method of the mixed liquid, it is possible to use various kinds of methods and, for example, an evaporation to dryness method, a spray drying method, a drum drying method, a flash drying method, a vacuum drying method, and the like may be mentioned. The types of the dryer to be used at drying are not particularly limited, but if it can achieve drying in the range of 80 to 300° C., a dry powder of a complex metal oxide according to the purpose can be obtained by appropriately changing the drying conditions in this range.

A pre-calcinated powder of a complex metal oxide (hereinafter referred to as pre-calcinated powder) can be obtained by calcinating the thus obtained dry powder at 300 to 600° C., preferably 400 to 500° C., in an air or nitrogen stream. Hereinafter, both of the dry powder and pre-calcinated powder are collectively referred to as catalyst powder.

The thus obtained catalyst powder can be used as a catalyst as it is but is shaped to be the catalyst of the invention in consideration of production efficiency and workability in the industrial production scale. The shape of the shaped one is not particularly limited and it may be a spherical shape, a cylinder shape, a ring shape, and the like. Although the shape should be selected in consideration of reaction results, production efficiency of catalysts, mechanical strength, and the like, the spherical shape is preferred. At shaping, a dry powder may be used, but it is preferred to use and shape a single pre-calcinated powder. However, separately prepared catalyst powders having different ingredient compositions may be mixed beforehand at any ratio and then shaped or a method of repeating an operation of supporting different kinds of catalyst powders on an inert support to coat-shape the catalyst powders as multi-layers may be employed. In this connection, at shaping, it is preferred to mix a shaping aid material such as crystalline cellulose and/or a strength enhancer such as ceramic whisker. The amount of each of the shaping aid and/or the strength enhancer to be used is preferably 30% by weight or less relative to the amount of the catalyst powder. Moreover, the shaping aid and/or the strength enhancer may be previously mixed with the above catalyst powder before shaping or may be added simultaneously to or before or after the addition of the catalyst powder to a shaping machine. Namely, the above shape of the shaped one and shaping method can be adopted as long as the shaped catalyst to be used in the reaction has finally catalyst physical properties and/or catalyst composition falling within the ranges of the invention.

At shaping as described above, the shaping method is not particularly limited, but, in the case of shaping into a cylinder shape and a ring shape, a tablet shaping machine, an extrusion shaping machine, and the like can be used. More preferably, it is the case of shaping into a spherical shape, and a catalyst powder may be shaped into a spherical shape on a shaping machine, but a method in which a catalyst powder (including a shaping aid and a strength enhancer according to need) is coat-shaped on a support such as an inert ceramic is preferred. The supporting method is not particularly limited as long as it is a tumbling granulation method, a method of using a centrifugal flow coating device, and a method such as a wash coat in which a catalyst powder can be homogeneously coat-shaped on the surface of the support. However, in consideration of production efficiency and the like of catalyst, it is preferred to use a method in which the catalyst powder is coat-shaped on the support by vigorously stirring the support charged into a fixed cylindrical container by repeated rotation movement and orbital movement of the support itself through rotation of a disk at a high speed by means of an apparatus having a flat or uneven disk on a bottom of the container, and adding thereto the catalyst powder and if necessary, the shaping aid and the strength enhancer. The relative centrifugal acceleration to be imparted at tumbling granulation is preferably 1G to 35G, more preferably 1.2G to 30G. Here, the relative centrifugal acceleration is a numerical value represented by the ratio of the intensity of centrifugal force per unit weight to gravitational acceleration at the time when the support is placed in the tumbling granulator and is rotated in the apparatus, and is represented by the following formula (2). The relative centrifugal acceleration increases in proportion to an absolute value of distance from the center of rotation of the apparatus and the square of rotation speed.

$$RCF=1118 \times r \times N^2 \times 10^{-8}$$ Formula (2)

In the formula (2), RCF represents relative centrifugal acceleration (G), r represents distance (cm) from the center of rotation, and N represents rotation speed (rpm).

At supporting, a binder is preferably used. Specific examples of the usable binder include water, ethanol, methanol, propanol, polyhydric alcohols, polyvinyl alcohol of a polymeric binder, an aqueous silica sol solution of an inorganic binder, and the like. Ethanol, methanol, propanol, and polyhydric alcohols are preferred, diols such as ethylene glycol and triols such as glycerin are more preferred, and an aqueous solution having a glycerin concentration of 5% by weight or more is particularly preferred. When an appropriate amount of the aqueous glycerin solution is used, shapability becomes good and a coat-shaped catalyst having a high mechanical strength and exhibiting a high activity is obtained.

The amount of the binder to be used is usually in an amount of 2 to 60 parts by weight based on 100 parts by weight of the catalyst powder and, in the case of the aqueous glycerin solution, the amount is preferably 10 to 30 parts by weight. At supporting, the binder may be mixed with the catalyst powder in advance or the binder may be added while supplying the catalyst powder to the tumbling granulator.

With regard to the size of the inert support, one having a diameter of about 2 to 15 mm is usually used and the catalyst powder is supported thereon. The support quantity is determined in consideration of conditions for using the catalyst, for example, space velocity and concentration of the raw material hydrocarbon.

Incidentally, the support amount of the catalyst powder in the coat-shaped catalyst is defined by the formula: weight of catalyst powder/(weight of catalyst powder+weight of support)×100. In this formula, the denominator may contain a shaping aid and/or a strength enhancer in some cases. When the support amount is too low, the activity becomes lower, and when the support amount is too high, the temperature of the catalyst layer becomes higher, and therefore they are not preferable. The support amount is preferably 10 to 70% by weight, more preferably 30 to 60% by weight.

The shaped catalyst is calcinated again before the catalyst is used in the reaction. The calcination temperature at the re-calcination is usually 400 to 700° C. and the calcination time is usually 3 to 30 hours, preferably 4 to 15 hours. They are appropriately set depending on the reaction conditions to be used. The atmosphere for the calcination at the re-calcination may be any of an air atmosphere and a nitrogen atmosphere but, industrially, an air atmosphere is preferred.

The physical properties are measured for the thus obtained shaped catalysts by various analyses. According to IUPAC, a pore of 2 nm or less, a pore of 2 nm to 50 nm, and a pore of 50 nm or more are defined as a micropore, a mesopore, and a macropore, respectively. When the ratio of micropores and mesopores to that of the total pores increases, the successive reaction is prone to occur since the active points come close to each other. On the other hand, when the ratio of macropores is large, the successive reaction is difficult to proceed and the selectivity for butadiene can be enhanced. The invention is characterized in that the selectivity for butadiene can be enhanced by using the catalyst having a pore volume of macropores of 80% or more, more preferably 90% or more based on the total pore volume. Moreover, when the total pore volume is low, a sufficient catalyst activity is not obtained and when the volume is too high, not only the above by-products increases but also the strength as catalyst becomes insufficient. Therefore, the invention is characterized in that the total pore volume is preferably 0.1 ml/g or more and 0.4 mug or less. With regard to the macropore of the invention, it is a value measured by a mercury intrusion method under the conditions of mercury surface tension of 480 dyn/cm and mercury contact angle of 140° by means of a mercury porosimeter (Pore Master 60-GT (Quanta Chrome Co.)). The upper limit of the macropore is a detection limit of the device. The term "having macropores" means the case of having pores of at least 0.01 ml/g in the pore volume obtained from the correlation graph in which the vertical axis is Normalized Volume [ml/g] showing the amount (ml) of mercury invading 1 g of a sample and the horizontal axis is Pore diameter.

In the process for producing butadiene according to the invention, n-butene is subjected to a gas-phase contact oxidative dehydrogenation using the above catalyst of the invention and molecular oxygen.

As the n-butene as a raw material, 1-butene alone or also a mixed butene containing at least two selected form 1-butene, trans-2-butene and cis-2-butene can be used. Further, as a raw material, butenes including n-butene from naphtha cracking furnace and fluid catalytic cracking equipment (FCC equipment) of oil can be also used. Besides, n-butene produced by a known method may be used. In addition, the unreacted raw material at the outlet of the reactor may be used as a reaction law material again.

As the molecular oxygen, air is usually used, but pure oxygen may be used.

The above raw material gas and molecular oxygen are preferably utilized as a mixed gas by diluting it with an inert gas. As the diluent gas, an inert gas such as nitrogen, helium, argon and carbon dioxide is used. A part of a non-condensable gas contained in the reaction gas may be used as a diluent gas by circulating it. In enhancing catalyst activity, selectivity and catalyst life, it is preferred that water vapor is contained in the diluent gas.

As the mixed gas, there may be mentioned a mixed gas containing n-butene in an amount of 1 to 16% by volume, preferably 3 to 12% by volume, molecular oxygen in an amount of 1 to 20% by volume, preferably 5 to 16% by volume, a diluent gas in an amount of 64 to 98% by volume, preferably 72 to 92% by volume, and water vapor in an amount of 60% by volume or less, based on 100% by weight of the mixed gas.

The gas-phase contact oxidative dehydrogenation of the invention is specifically performed by introducing a mixed gas containing at least n-butene and molecular oxygen in the presence of the above catalyst of the invention at a temperature range of 250 to 450° C., preferably 280 to 400° C. under a pressure of ordinary pressure to 10 atm (a gauge pressure) at a space velocity per an unit volume of the catalyst of 300 to 5,000/hr, preferably 500 to 3,500/hr.

The type of the reactor for producing butadiene in the invention may be any type of a fluidized bed, a moving bed and a fixed bed, but the fixed bed is preferred in the case of using the catalyst of the invention.

In the case of using the catalyst of the invention in a fixed bed, catalysts having various physical properties, activities, support amounts and particle sizes may be used in the reaction tube.

The local high temperature part (PT) in the catalyst layer during the reaction becomes a problem when operating stably a plant. As this index, it can be expressed using the temperature difference ($\Delta T$) obtained by subtracting the set temperature from the PT. It is preferred that $\Delta T$ is smaller as possible. In general, in the complex metal oxide having Mo as a main ingredient, Mo is scattered or the crystal phase is changed into $MoO_3$ by the exposure of the catalyst to a high temperature, so that it is known that the catalyst is deteriorated. Namely, when there is a part at which $\Delta T$ is especially large at the reaction, the catalyst at that part is deactivated and thus the catalyst life is shortened. Further, in consideration of a stable operation, it is important that the change from $\Delta T$ within one hour after the start of the reaction to $\Delta T$ after the elapse of two hours or more is small. In the case where the change is small, since the start-up in the plant is performed speedily, it becomes advantageous economically. For the purpose of mitigating the $\Delta T$ or the changes in PT from the start of the reaction up to a stable state, the catalyst may be filled together with an inert material, and as a result, catalyst layers formed by dividing into a plurality in the raw material gas flow direction of the reaction tube is provided. The inert material is not particularly limited as long as it is substantially inert to the reaction, but silica, alumina, titania, or composites thereof, and the like are included. In the case of filling together with an inert material, it is possible to provide a catalyst having different activities for each of the divided catalyst layers.

EXAMPLES

The following will more specifically describe the present invention with reference to Examples but the invention should not be construed as being limited to these Examples. The conversion of n-butene, selectivity for butadiene and yield of butadiene in Examples are each defined as follows.

Conversion of n-butene=(Number of moles of reacted n-butene)/(Number of moles of supplied n-butene)×100

Selectivity for butadiene=(Number of moles of formed butadiene)/(Number of moles of reacted n-butene)×100

Yield of butadiene=(Conversion of n-butene/100)× (Selectivity for butadiene/100)×100

Example 1

<Catalyst>

While heating and stirring 3,000 parts by weight of distilled water, 423.8 parts by weight of ammonium molybdate and 1.64 parts by weight of potassium nitrate were dissolved therein to obtain an aqueous solution (A1). Separately, 302.7 parts by weight of cobalt nitrate, 162.9 parts by weight of nickel nitrate, and 145.4 parts by weight of ferric nitrate were dissolved in 1,000 parts by weight of distilled water to prepare an aqueous solution (B1), and 164.9 parts by weight of bismuth nitrate was dissolved in 200 parts by weight of distilled water, which had been acidified by adding 42 parts by weight of conc. nitric acid, to prepare an aqueous solution (C1). Then, (B1) and (C1) were sequentially mixed into the above aqueous solution (A1) with vigorous stirring and the formed suspension was dried by means of a spray dryer and calcinated at 440° C. for 6 hours to obtain a pre-calcinated powder (D1). The composition ratio of the catalyst-active ingredient excluding oxygen at this time was as follows: Mo=12, Bi=1.7, Ni=2.8, Fe=1.8, Co=5.2 and K=0.15 in terms of atomic ratio.

Thereafter, using a powder obtained by mixing 5 parts by weight of crystalline cellulose into 100 parts by weight of the pre-calcinated powder and an inert support (a spherical material containing alumina and silica as main ingredients and having a diameter of 4.5 mm), the weight of the support and the weight of the pre-calcinated powder for use in shaping were adjusted so that the support amount became a ratio of 50% by weight. Using a 20% by weight aqueous glycerin solution as a binder, a coat-shaped catalyst (E1) was obtained by supporting and shaping into a spherical shape having a diameter of 5.2 mm by means of a tumbling granulator.

For the support shaping, a cylindrical shaping machine having a diameter of 23 cm was used and the number of rotations of the base plate was controlled to 260 rpm. The relative centrifugal acceleration on this occasion was 8.7G.

The coat-shaped catalyst (E1) was calcinated at a calcination temperature of 530° C. for 4 hours under an air atmosphere to obtain a catalyst (F1).

<Catalyst Analysis>

The total pore volume of the above catalyst (F1) was 0.24 ml/g and the ratio of the pore volume of macropores was 99%.

<Dehydrogenation Reaction Test>

A silica-alumina sphere having a diameter of 5.2 mm and the above catalyst (F1) each were sequentially packed in 30 cm and 8 cm into a stainless steel-made reaction tube having an inner diameter of 22.2 mm, in which a thermocouple to measure the catalyst layer temperature was installed at the axis of the tube, from the raw material gas inlet of the reaction tube. The temperature of the reaction bath was set at 320° C. A mixed gas having a molar ratio of n-butene:air:water=1:10:5, in which the supply amount was set to become a space velocity of 1440 h$^{-1}$, was introduced into the reaction tube to carry out a dehydrogenation reaction. In addition, as the n-butene, a 1-butene gas of 99% purity was used. Then, the outlet gas after the elapse of two hours from the start of the reaction was analyzed by means of a gas chromatography. The conversion of n-butene, selectivity for butadiene, and yield of butadiene are shown in Table 1. Further, ΔT immediately after the start of the reaction and ΔT after the elapse of two hours are also shown in Table 1.

From Table 1, even after the elapse of two hours from the start of the reaction, it was seen that the conversion of n-butene was 99.3% and the yield of butadiene was 89.0% and thus a high conversion and a high yield were achieved. It was also seen that ΔT immediately after the start of the reaction was 42.8° C. and ΔT after the elapse of two hours was 39.2° C. and thus a large temperature change was not observed and ΔT was stable from the beginning of the reaction.

From the above results, it can be seen that butadiene can be obtained from n-butene in a high conversion and a high yield for a long period of time, and a stable operation can be performed from the beginning of the reaction.

TABLE 1

| Reaction time (hr) | Conversion of n-butene (%) | Selectivity for butadiene (%) | Yield of butadiene (%) | ΔT (° C.) |
|---|---|---|---|---|
| At the start of reaction | — | — | — | 42.8 |
| 2 | 99.3 | 89.6 | 89 | 39.2 |

Comparative Example 1

<Catalyst>

A mixed powder was obtained by mixing 100 parts by weight of the pre-calcinated powder (D1) with 10 parts by weight of crystalline cellulose and 10 parts by weight of YB-155 (a shaping aid for extrusion) manufactured by Yuken Industry Co., Ltd. To the mixed powder was mixed 100 parts by weight of AEROSIL OX50 manufactured by Nippon Aerosil Co., Ltd., and the whole was extruded so as to be a ring shape to obtain an extrusion-shaped catalyst (E2). The outer diameter/inner diameter/length (mm) of the resulting shaped catalyst (E2) was 5.4/3.6/5.0.

The extrusion-shaped catalyst (E2) was calcinated under the same conditions as in Example 1 to obtain a catalyst (F2).

<Catalyst Analysis>

The total pore volume of the above catalyst (F2) was 0.42 ml/g and the ratio of the pore volume of macropores was 78%.

<Dehydrogenation Reaction Test>

A dehydrogenation reaction test was carried out in the same manner as Example 1 except that the catalyst (F2) was used. Then, the outlet gas after the elapse of two hours from the start of the reaction was analyzed by means of a gas chromatography. The results of the reaction are shown in Table 2 in the same manner as Example 1.

From Table 2, it can be seen that ΔT is 97.4° C. at the beginning of the reaction and is 50° C. or more higher than that in Example 1 and thus particularly large heat generation occurs. Even after two hours from the start of the reaction, ΔT is 10° C. or more higher than that in Example 1. Therefore, since the catalyst is exposed to higher temperature, the case is disadvantageous in catalyst life. ΔT immediately after the start of the reaction and ΔT after the elapse of two hours are 97.4° C. and 55.8° C., respectively and a large temperature change is observed immediately after the reaction, so that it is surmised that the operation in plant is very difficult.

Moreover, it was seen that the yield of butadiene after the elapse of two hours was 2.5% lower than that in Example 1. This is because a successive reaction proceeds to increase CO and CO$_2$ and the selectivity for butadiene is decreased. Since the amount of the active ingredient of the catalyst is equal in Comparative Example 1 and Example 1, it is surmised that a difference in the ratio of macropores to mesopores in the pore volume remarkably influences the degree of the successive reaction. When the successive reaction increases, the heat of reaction owing to the reaction becomes large and as a result, ΔT becomes larger.

Therefore, by using a catalyst having a large ratio of pore volume of macropores of the invention, ΔT could be suppressed and the yield of butadiene could be enhanced.

TABLE 2

| Reaction time (hr) | Conversion of n-butene (%) | Selectivity for butadiene (%) | Yield of butadiene (%) | ΔT (° C.) |
|---|---|---|---|---|
| At the start of reaction | — | — | — | 97.4 |
| 2 | 99.3 | 87.1 | 86.5 | 55.8 |

Comparative Example 2

<Catalyst>

A mixed powder was obtained by mixing 100 parts by weight of the pre-calcinated powder (D1) with 5 parts by weight of crystalline cellulose and 5 parts by weight of YB-155 (a shaping aid for extrusion) manufactured by Yuken Industry Co., Ltd. To the mixed powder was mixed 20 parts by weight of AEROSIL 200 manufactured by Nippon Aerosil Co., Ltd., and the whole was extruded so as to be a ring shape to obtain an extrusion-shaped catalyst (E3). The outer diameter/inner diameter/length (mm) of the resulting shaped catalyst (E3) was 5.4/3.6/5.0.

The extrusion-shaped catalyst (E3) was calcinated under the same conditions as in Example 1 to obtain a catalyst (F3).

<Catalyst Analysis>

The total pore volume of the above catalyst (F3) was 0.47 ml/g and the ratio of the pore volume of macropores was 79%.

<Dehydrogenation Reaction Test>

The catalyst (F3) and an inactive substance were mixed so that the amount of the active ingredient per unit volume became equal to that in Example 1 and Comparative Example 1 and the same volume as in Example 1 and Comparative Example 1 was packed. As the inert material, a silica-alumina sphere having a diameter of 5.2 mm was used. Except for the above, a dehydrogenation reaction test was carried out in the same manner as Example 1. Then, the outlet gas after the elapse of two hours from the start of the reaction was analyzed by means of a gas chromatography. The results of the reaction are shown in Table 3.

From the result of Table 3, the heat generation at the reaction could be suppressed by diluting the catalyst with the inert material but the conversion of n-butene decreased by 5.2% after the elapse of two hours from the start of the reaction although the amount of the active ingredient was equal to that in Example 1. Therefore, effects equal to those exhibited by the catalyst of the invention cannot be exhibited by simply diluting the catalyst with the inert material.

TABLE 3

| Reaction time (hr) | Conversion of n-butene (%) | Selectivity for butadiene (%) | Yield of butadiene (%) | ΔT (° C.) |
|---|---|---|---|---|
| At the start of reaction | — | — | — | 37.1 |
| 2 | 94.1 | 89 | 83.7 | 30.7 |

Example 2

<Catalyst>

While heating and stirring 3,000 parts by weight of distilled water, 750 parts by weight of ammonium molybdate and 13.8 parts by weight of cesium nitrate were dissolved therein to obtain an aqueous solution (A4). Separately, 695.5 parts by weight of cobalt nitrate, 103 parts by weight of nickel nitrate, and 286 parts by weight of ferric nitrate were dissolved in 1,000 parts by weight of distilled water to prepare an aqueous solution (B4), and 291.8 parts by weight of bismuth nitrate was dissolved in 300 parts by weight of distilled water, which had been acidified by adding 73 parts by weight of conc. nitric acid, to prepare an aqueous solution (C4). Then, (B4) and (C4) were sequentially mixed into the above aqueous solution (A4) with vigorous stirring and the formed suspension was dried by means of a spray dryer and calcinated at 460° C. for 5 hours to obtain a pre-calcinated powder (D4). The composition ratio of the catalyst-active ingredient excluding oxygen at this time was as follows: Mo=12, Bi=1.7, Ni=1.0, Fe=2.0, Co=6.8 and Cs=0.20 in terms of atomic ratio.

Thereafter, using a powder obtained by mixing 5 parts by weight of crystalline cellulose into 100 parts by weight of the pre-calcinated powder and an inert support (a spherical material containing alumina and silica as main ingredients and having a diameter of 4.0 mm), the weight of the support and the weight of the pre-calcinated powder for use in shaping were adjusted so that the support amount became a ratio of 50% by weight. Using a 20% by weight aqueous glycerin solution as a binder, a coat-shaped catalyst (E4) was obtained by supporting and shaping into a spherical shape having a diameter of 4.4 mm.

For the support shaping, a cylindrical shaping machine having a diameter of 23 cm was used and the number of rotations of the base plate was controlled to 260 rpm. The relative centrifugal acceleration at this time was 8.7G.

The coat-shaped catalyst (E4) was calcinated at 520° C. for 4 hours to obtain a catalyst (F4).

<Catalyst Analysis>

The total pore volume of the above catalyst (F4) was 0.25 ml/g and the ratio of the pore volume of macropores was 100%.

<Dehydrogenation Reaction Test>

A dehydrogenation reaction test was carried out in the same manner as Example 1 except that the catalyst (F4) was used and the reaction temperature was 330° C. Then, the outlet gas after the elapse of two hours from the start of the reaction was analyzed by means of a gas chromatography. The results of the reaction are shown in Table 4 in the same manner as Example 1.

From the results of Table 4, even in the catalyst (F4) having a composition different from that of the catalyst (F1), after the elapse of two hours from the start of the reaction, it was seen that the conversion of n-butene was 98.9% and the yield of butadiene was 91.0% and thus a high conversion and a high yield were achieved.

Moreover, ΔT at the beginning of the reaction was 26.7° C. and it is seen that the heat generation is a little. ΔT after the elapse of two hours from the start of the reaction is 27.6° C.

Therefore, similarly to Example 1, it was seen that a large temperature change was not observed and the temperature was stable from the beginning of the reaction.

TABLE 4

| Reaction time (hr) | Conversion of n-butene (%) | Selectivity for butadiene (%) | Yield of butadiene (%) | ΔT (° C.) |
|---|---|---|---|---|
| At the start of reaction | — | — | — | 26.7 |
| 2 | 98.9 | 92.0 | 91.0 | 27.6 |

From the above results, a catalyst wherein the ratio of the pore volume of macropores is 80% or more can suppress a heat generation behavior and be stably used, can be used at a high conversion of n-butene even at a little ΔT, and can maintain a high yield of butadiene, so that the catalyst is industrially very useful.

While the invention has been described in detail and with reference to specific embodiments thereof, it will be apparent to one skilled in the art that various changes and modifications can be made therein without departing from the spirit and scope thereof.

The present application is based on Japanese Patent Application No. 2012-098259 filed on Apr. 23, 2012, and the contents are incorporated herein by reference. Also, all the references cited herein are incorporated as a whole.

INDUSTRIAL APPLICABILITY

The catalyst of the present invention is used in a process for stably producing butadiene from n-butene from the beginning of the reaction.

The invention claimed is:

1. A shaped catalyst of a complex metal oxide having molybdenum as an essential ingredient, which is a shaped catalyst used in production of butadiene by a gas-phase contact oxidative dehydrogenation reaction of n-butene in the presence of molecular oxygen, wherein pore volume of macropores of the shaped catalyst is 80% or more based on a total pore volume, wherein the shaped catalyst is a spherical coat-shaped catalyst in which the complex metal oxide is supported on an inert spherical support.

2. The shaped catalyst according to claim 1, wherein the pore volume of macropores of the shaped catalyst is 90% or more based on the total pore volume.

3. The shaped catalyst according to claim 1, wherein the total pore volume is 0.1 ml/g or more and 0.4 ml/g or less.

4. The shaped catalyst according to claim 1,
wherein the complex metal oxide has a composition represented by the following formula (1):

$$Mo_aBi_bNi_cCo_dFe_fX_gY_hO_x \hspace{2cm} \text{Formula (1)}$$

wherein Mo, Bi, Ni, Co, Fe and O represents molybdenum, bismuth, nickel, cobalt, iron and oxygen, respectively;

X represents at least one element selected from the group consisting of tungsten, antimony, tin, zinc, chromium, manganese, magnesium, silicon, aluminum, cerium, tellurium, boron, germanium, zirconium and titanium;

Y represents at least one element selected from the group consisting of potassium, rubidium, calcium, barium, thallium and cesium;

a, b, c, d, f, g, h and x represents numbers of atoms of molybdenum, bismuth, nickel, cobalt, iron, X, Y and oxygen, respectively, and a=12, b=0.1 to 7, c+d=0.5 to 20, f =0.5 to 8, g=0 to 2, h=0.005 to 2, and x=a value determined depending on oxidation states of individual elements.

5. The shaped catalyst according to claim 1, wherein powder of the complex metal oxide is supported by a tumbling granulation method.

6. A process for producing the coat-shaped catalyst according to claim 1, wherein powder of the complex metal oxide is supported by a tumbling granulation method.

7. A process for producing butadiene by using the shaped catalyst according to claim 1 and subjecting n-butene to gas-phase contact oxidative dehydrogenation in the presence of molecular oxygen.

8. The process for producing butadiene according to claim 7, wherein a change between $\Delta T$ within one hour from start of reaction and $\Delta T$ after two hours is 20° C. or less.

9. The process for producing butadiene according to claim 7, wherein a shaped catalyst of a complex metal oxide having molybdenum as an essential ingredient, which is a shaped catalyst used in production of butadiene by a gas-phase contact oxidative dehydrogenation reaction of n-butene in the presence of molecular oxygen, wherein pore volume of macropores of the shaped catalyst is 80% or more based on a total pore volume, is used, and a change between $\Delta T$ within one hour from start of reaction and $\Delta T$ after two hours is 10° C. or less.

* * * * *